(12) United States Patent
Everett et al.

(10) Patent No.: US 9,713,594 B2
(45) Date of Patent: Jul. 25, 2017

(54) METHODS FOR MAKING PHARMACEUTICAL SOLID DOSAGE FORMS OF SPRAY-DRIED DISPERSIONS

(71) Applicant: Bend Research, Inc., Bend, OR (US)

(72) Inventors: Jason A. Everett, San Diego, CA (US); Randy J. Wald, Bend, OR (US); Sanjay Konagurthu, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

(21) Appl. No.: 14/426,647

(22) PCT Filed: Sep. 5, 2013

(86) PCT No.: PCT/US2013/058173
§ 371 (c)(1),
(2) Date: Mar. 6, 2015

(87) PCT Pub. No.: WO2014/042945
PCT Pub. Date: Mar. 20, 2014

(65) Prior Publication Data
US 2015/0216813 A1 Aug. 6, 2015

Related U.S. Application Data

(60) Provisional application No. 61/699,674, filed on Sep. 11, 2012.

(51) Int. Cl.
| | |
|---|---|
| *A61K 9/10* | (2006.01) |
| *A61K 9/50* | (2006.01) |
| *A61K 9/16* | (2006.01) |
| *A61K 9/20* | (2006.01) |
| *A61K 31/4166* | (2006.01) |

(52) U.S. Cl.
CPC .............. *A61K 9/5089* (2013.01); *A61K 9/10* (2013.01); *A61K 9/1611* (2013.01); *A61K 9/1652* (2013.01); *A61K 9/1694* (2013.01); *A61K 9/2009* (2013.01); *A61K 9/2054* (2013.01); *A61K 9/2077* (2013.01); *A61K 9/2095* (2013.01); *A61K 31/4166* (2013.01)

(58) Field of Classification Search
CPC ............................. A61K 9/2095; A61K 9/2077
See application file for complete search history.

(56) References Cited

U.S. PATENT DOCUMENTS 8,722,684 B2 * 5/2014 Bang-Andersen . C07D 295/096
424/489

2009/0326078 A1* 12/2009 Remon ................ A61K 9/2095
514/778
2012/0014912 A1* 1/2012 Dokou ................ A61K 9/0056
424/85.4
2012/0034283 A1* 2/2012 Sunder ................ C11D 3/1246
424/401

FOREIGN PATENT DOCUMENTS

| WO | WO 01/68092 | 9/2001 |
|---|---|---|
| WO | WO 2007/109605 | 9/2007 |
| WO | WO 2012/009503 | 1/2012 |
| WO | WO 2012/027247 | 3/2012 |

OTHER PUBLICATIONS

Ferrari, F. et al. AAPS PharmSciTech, Feb. 2004, 5(4).*
Pingali, K. et al. Int. J. Pharm. May 16, 2011; 409(0): 269-277.*
International Search Report and Written Opinion for related International Application No. PCT/US2013/058173, 9 pages, mailed Jan. 31, 2014.
Ghoroi, C. et al., "Multi-faceted characterization of pharmaceutical powders to discern the influence of surface modification," *Powder Technology*, vol. 236, Special Issue: Pharmaceutical Powders, pp. 63-74 (Feb. 2013).
Han, X. et al., "Simultaneous micronization and surface modification for improvement of flow and dissolution of drug particles," *International Journal of Pharmaceutics*, vol. 415, Issues 1-2 pp. 185-195 (Aug. 2011).
Huang, Z., et al., "Improved blend and tablet properties of fine pharmaceutical powders via dry particle coating," *International Journal of Pharmaceutics*, vol. 478, Issue 2, pp. 447-455 (Jan. 2015).
Jallo, L., et al., "Improvement of flow and bulk density of pharmaceutical powders using surface modification," *International Journal of Pharmaceutics*, vol. 423, Issue 2, pp. 213-225 (Feb. 2012).
Mullarney, M., et al., "Applying dry powder coatings to pharmaceutical powders using a comil for improving powder flow and bulk density," *Powder Technology*, vol. 212, Issue 3, pp. 397-402, (Oct. 2011).
Yang, J. et al., "Dry particle coating for improving the flowability of cohesive powders," *Powder Technology*, vol. 158, Issues 1-3, pp. 21-33 (Oct. 2005).

* cited by examiner

*Primary Examiner* — Gina Justice
(74) *Attorney, Agent, or Firm* — Klarquist Sparkman, LLP

(57) ABSTRACT

An exemplary method comprises providing a spray-dried dispersion comprising particles, the particles comprising an active agent and a polymer, the dispersion particles having an average particle diameter of less than 50 µm. An ordered mixture is formed by high-shear mixing the dispersion with a powdered glidant, wherein the average particle diameter of the glidant is less than or equal to one fifth the average particle diameter of the dispersion after high-shear mixing. The dosage forms are formed by at least one of directly compressing the ordered mixture to form a tablet and encapsulating the ordered mixture to form a capsule.

18 Claims, 1 Drawing Sheet

| BLENDING (SDD AND GLIDANT) |
|---|
| LDPE bag or Equivalent and #30 mesh screen |
| 25%A Phenytoin:HPMCAS-MG SDD and Colloidal Silicon Dioxide |
| Blend time: 2 minutes |
| Blender speed: Manual Bag blend by hand |

↓

| BLENDING (FILLERS AND DISINTEGRANT) |
|---|
| Turbula Mixer with appropriately sized bottle or Equivalent |
| 25%A Phenytoin:HPMCAS-MG SDD with Colloidal Silicon Dioxide, Microcrystalline Cellulose, Lactose Monohydrate, and Croscarmellose Sodium |
| Blend time: 15 minutes |
| Blender speed: Default Setting |

↓

| HIGH-SHEAR MIXING (CONE-MILL PROCESSING) |
|---|
| Comil 193 AS or equivalent |
| Blend from Previous Step |
| Screen: 0.032-inch Rasping screen |
| Impeller: 1601 |
| Impeller speed: 2000 rpm |

↓

| BLENDING (LUBRICANT) |
|---|
| Turbula Mixer with appropriately sized bottle or Equivalent and #30 mesh screen |
| Blend from Previous Step and Magnesium Stearate |
| Blend time: 5 minutes |
| Blender speed: Default |

↓

| TABLET COMPRESSING (INCLUDING DEDUSTING AND METAL CHECKING) |
|---|
| Manesty F Press or Equivalent |
| Final Blend from Previous Step |
| (See Table 4 for Operational Parameters) |

METHODS FOR MAKING PHARMACEUTICAL SOLID DOSAGE FORMS OF SPRAY-DRIED DISPERSIONS

CROSS REFERENCE TO RELATED APPLICATIONS

This is the U.S. National Stage of International Application No. PCT/US2013/058173, filed Sep. 5, 2013, which was published in English under PCT Article 21(2), which in turn claims the benefit of U.S. Provisional Application No. 61/699,674, filed Sep. 11, 2012. The provisional application is incorporated by reference herein in its entirety.

FIELD

The present disclosure relates to methods for making pharmaceutical solid dosage forms from spray-dried dispersions, using high-shear mixing.

BACKGROUND

Spray drying can result in a powdered dispersion having poor bulk flow properties. The poor bulk flow properties create a need to granulate the powdered dispersion prior to incorporating the powdered dispersion into a solid dosage form, such as tablets and capsules, which granulation is costly and time consuming. Without granulation, the powdered dispersion can exhibit poor and inconsistent flow out of hoppers as well as inconsistent tablet die or capsule filling. Granulation processes can include wet or dry granulation, such as dry granulation via roller compaction.

SUMMARY

Disclosed herein are methods for making pharmaceutical solid dosage forms from spray-dried dispersions, using high-shear mixing.

An exemplary method for forming a pharmaceutical dosage form comprises: providing a spray-dried dispersion comprising particles wherein the particles comprise an active agent and a polymer, the dispersion having an average particle diameter of less than 50 µm; forming an ordered mixture by high-shear mixing a blend comprising the dispersion and a powdered glidant, the glidant having an average particle diameter of less than or equal to one-fifth the average particle diameter of the dispersion after high-shear mixing; and forming the pharmaceutical dosage form by at least one of directly compressing the ordered mixture to form a tablet and encapsulating the ordered mixture to form a capsule.

In some embodiments, the glidant in the ordered mixture has an average particle diameter of less than or equal to one-tenth of the average particle diameter of the dispersion in the ordered mixture after high-shear mixing. In some embodiments, the glidant in the ordered mixture has an average particle diameter of less than or equal to one-twentieth of the average particle diameter of the dispersion in the ordered mixture after high-shear mixing.

In some embodiments, the ordered mixture is an interactive mixture.

In some embodiments, the dispersion has an average particle diameter of less than 30 µm prior to high-shear mixing. In some embodiments, the dispersion has an average particle diameter of less than 20 µm prior to high-shear mixing.

In some embodiments the dispersion comprises at least 50% of the tablet by weight.

In some embodiments the high-shear mixing has a Froude Number greater than or equal to 1.

In some embodiments, the blend further comprises at least one other excipient.

Another exemplary method of preparing a pharmaceutical dosage form comprises: providing a spray-dried dispersion comprising particles wherein the particles comprise an active agent and a polymer, the dispersion having an average particle diameter of less than 50 µm; forming an ordered mixture comprising the dispersion and a glidant using high-shear mixing, the ordered mixture having a Carr's Index of less than 40%; and forming the pharmaceutical dosage form by directly compressing the ordered mixture to form a tablet or encapsulating the ordered mixture to form a capsule.

In some embodiments, the ordered mixture has a Can's Index of less than or equal to 35%.

In some embodiments, the glidant in the ordered mixture has an average particle diameter of less than or equal to one-fifth of the average particle diameter of the dispersion in the ordered mixture after high-shear mixing.

In some embodiments, the glidant in the ordered mixture has an average particle diameter of less than or equal to one-tenth of the average particle diameter of the dispersion in the ordered mixture after high-shear mixing. In some embodiments, the glidant in the ordered mixture has an average particle diameter of less than or equal to one-twentieth of the average particle diameter of the dispersion in the ordered mixture after high-shear mixing.

In some embodiments, the ordered mixture further comprises at least one other excipient.

In some embodiments, the ordered mixture is an interactive mixture.

Another exemplary method for making a tablet comprises: spray drying a first powder, the first powder comprising a dispersion of an active agent and a polymer, the first powder having an average particle diameter of less than 50 µm and a bulk specific volume greater than or equal to 3 cc/g; high-shear mixing the first powder with a second powder to form an ordered mixture; and directly compressing the blend to form a tablet.

In some embodiments, the second powder has a bulk specific volume greater than 20 cc/g.

In some embodiments, the first powder has an average particle diameter of less than 30 µm. In some embodiments, the first powder has an average particle diameter of less than 20 µm.

In some embodiments, the first powder has a bulk specific volume greater than or equal to 5 cc/g.

In some embodiments, the second powder has a specific surface area of from 50 m²/g to 600 m²/g.

Another exemplary method for forming a pharmaceutical dosage form comprises: providing a spray-dried amorphous dispersion comprising particles, the particles comprising an active agent and a polymer, the dispersion having an average particle diameter of less than 50 µm; forming a blend comprising the dispersion and a powdered glidant using high-shear mixing, the high-shear mixing having a Froude Number greater than 0.2; and forming the pharmaceutical dosage form by at least one of directly compressing the blend to form a tablet and encapsulating the blend to form a capsule.

In some embodiments, the Froude Number is greater than 1.

In some embodiments, the high-shear mixing comprises an impeller rotation rate of at least 1000 RPM. In some embodiments, the high-shear mixing comprises an impeller rotation rate of at least 2000 RPM.

In some embodiments, the blend comprises an ordered mixture or an interactive mixture of the dispersion and the glidant.

In some embodiments, the glidant comprises an average particle diameter less than or equal to one-fifth the average particle diameter of the dispersion after the high shear mixing.

In some embodiments, the high-shear mixing reduces the average particle size of the glidant to less than or equal to 50 nm.

Another exemplary method for forming a pharmaceutical tablet comprises: providing a spray-dried powdered dispersion comprising particles, the particles comprising an active agent and a polymer, the dispersion having an average particle diameter of less than 50 µm; forming an ordered mixture by high-shear mixing a blend comprising the dispersion and a powdered glidant; and directly compressing the ordered mixture to form an at least 400 mg tablet, wherein the tablet comprises at least 50% of the dispersion by weight, and wherein the tablet is substantially completely disintegratable in 10 minutes or less when placed in 700 mL of a gastric buffer comprising 0.01 M HCL, the gastric buffer having a pH of 2.2 and a temperature of 37.5° C.

In some embodiments, the tablet comprises at least 70% of the dispersion by weight. In some embodiments, the tablet comprises at least 80% of the dispersion by weight.

In some embodiments, the tablet is substantially completely disintegrated in 5 minutes or less when placed in 700 mL of a gastric buffer comprising 0.01 M HCL, the gastric buffer having a pH of 2.2 and a temperature of 37.5° C. In some embodiments, the tablet is substantially completely disintegrated in 1 minute or less when placed in 700 mL of a gastric buffer comprising 0.01 M HCL, the gastric buffer having a pH of 2.2 and a temperature of 37.5° C.

Another exemplary method comprises: spray drying a liquid solution to form a first powder comprising a dispersion of an active agent and a polymer, the first powder having an average particle diameter of less than 50 µm and a bulk specific volume greater than 3 cc/g; forming an ordered mixture of the first powder with a second powder using high-shear mixing, the second powder having a surface area of at least 50 m$^2$/g, the high-shear mixing having a Froude Number of at least 1, the ordered mixture having a Carr's Index of less than 40%; and directly compressing the blend into a pharmaceutical tablet, the pharmaceutical tablet comprising at least 70% dispersion by weight, and wherein the pharmaceutical tablet is substantially completely disintegrated in less than 10 minutes when placed in 700 mL of a gastric buffer comprising 0.01 M HCL, the gastric buffer having a pH of 2.2 and a temperature of 37.5° C.

In some embodiments, the second powder has a bulk specific volume greater than 20 cc/g.

In some embodiments, forming the ordered mixture further comprises:
prior to the high-shear mixing, low-shear mixing the second powder with a portion of the first powder.

In some embodiments, the portion of the first powder in the ordered mixture comprises 3 to 10 times the weight of the second powder in the ordered mixture.

In some embodiments, the second powder comprises colloidal silicon dioxide, fumed silica, CAB-O-SIL® M5-P or mixtures thereof.

In some embodiments, the pharmaceutical tablet comprises 1% to 1.5% of the second powder by weight.

In some embodiments, the directly compressing comprises applying a compression force of from 20 kN to 25 kN.

In some embodiments, the pharmaceutical tablet has a hardness of from 16 kP to 20 kP.

In some embodiments, the ordered mixture is formed in a continuous process and compressing the ordered mixture into the pharmaceutical tablet is performable in a repeating process simultaneous with forming the ordered mixture.

An exemplary pharmaceutical tablet can be formed according to any of the methods described herein.

BRIEF DESCRIPTION OF THE DRAWING

FIG. 1 outlines an embodiment of the disclosed processes for blending and compression.

DETAILED DESCRIPTION

Various exemplary methods for preparing pharmaceutical solid dosage forms from spray-dried dispersions, using high-shear mixing are disclosed herein. The following description is exemplary in nature and is not intended to limit the scope, applicability, or configuration of the invention in any way. Various changes to the described methods may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items absent specific contrary language.

Unless otherwise indicated, all numbers expressing quantities of ingredients, properties such as molecular weight, average particle size, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Although the operations of exemplary embodiments of the disclosed methods may be described in a particular, sequential order for convenient presentation, it should be understood that certain of the disclosed embodiments can encompass an order of operations other than the particular, sequential order disclosed. For example, operations described sequentially may in some embodiments be rearranged or performed concurrently. Further, descriptions and disclosures provided in association with one particular embodiment are not limited to that embodiment, and may be applied to other embodiments disclosed.

As used herein, the term "spray-dried dispersion" or "spray-dried powdered dispersion" means a product of a spray-drying process wherein the product comprises a dispersion of at least one active agent and at least one excipient, such as a polymer.

As used herein, the term "solid amorphous dispersion" means a dispersion comprising an active agent and a polymer, wherein the active agent is substantially, or almost completely amorphous or non-crystalline. A solid amorphous dispersion may also be termed a "molecular dispersion" in which at least one component is homogeneously or substantially homogeneously dispersed on a molecular level throughout another component. A molecular dispersion is also known as a solid solution.

As used herein, the term "active agent" means a drug, medicament, pharmaceutical, therapeutic agent, nutraceutical, nutrient, or other compound. The active agent may be a "small molecule," generally having a molecular weight of 2000 Daltons or less. The active agent may also be a "biological active." Biological actives include proteins, antibodies, antibody fragments, peptides, oligonucleotides, vaccines, and various derivatives of such materials. In one embodiment, the active agent is a small molecule. In another embodiment, the active agent is a biological active. In still another embodiment, the active agent is a mixture of a small molecule and a biological active. In yet another embodiment, the compositions made by certain of the disclosed processes comprise two or more active agents.

As used herein, the term "excipient" means a substance that may be beneficial to include in a composition with an active agent. The term "excipient" includes inert substances as well as functional excipients that may result in beneficial properties of the composition. Exemplary excipients include but are not limited to polymers, glidants, sugars, salts, buffers, fats, fillers, disintegrating agents, binders, surfactants, high surface area substrates, flavorants, carriers, matrix materials, and so forth. Specific examples can include microcrystalline cellulose, lactose monohydrate, croscarmellose sodium, magnesium stearate, and derivatives and mixtures thereof.

For spray-dried dispersions, comprising an active agent and a polymer, exemplary polymers include polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly (lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), cellulose acetate phthalate (CAP), cellulose acetate trimellitate (CAT), ethyl cellulose, cellulose acetate, cellulose butyrate, cellulose acetate butyrate, dextran polymer derivatives, and pharmaceutically acceptable forms, derivatives, and mixtures thereof.

As used herein, the terms "powder" and "powdered" mean dry, amorphous solids composed of a plurality of fine, loose particles.

As used herein, the term "glidant" means a substance that, when added to a powder, improves the flowability of the powder, such as by reducing inter-particle friction. Exemplary glidants include but are not limited to colloidal silicas, colloidal silicon dioxide, fumed silica, CAB-O-SIL® M-5P, AEROSIL®, talc, starch, and magnesium aluminum silicates.

As used herein, the term "Froude Number" means a dimensionless parameter "Fr" used to characterize a mixing process, such that $Fr=V^2/gD_c$, where V is the characteristic velocity of the particles in a mixing chamber, $D_c$ is the characteristic diameter of the chamber, and g is the acceleration due to Earth's gravity. For a rotating agitator, such as an impeller, the characteristic velocity may be defined as $V=\pi D_a N$, where $D_a$ is the diameter of the agitator and N is the agitator rotation rate in revolutions per unit time.

As used herein, the term "high-shear mixing" means a powder mixing process characterized by a Froude Number within a specified range, such as greater than 0.01, greater than 0.1, greater than 0.2, greater than 0.5, greater than 1, greater than 10, and/or greater than 20, for example. Where the Froude Number is not specified, the term "high-shear mixing" means a powder mixing process characterized by a Froude Number of at least 1. The term "high-shear mixing" does not include high-shear granulation or dissolving or dispersing a solid in a liquid.

As used herein, the term "low-shear mixing" means a conventional mixing process that is not high-shear mixing.

As used herein, the term "ordered mixture" means a mixture of powders having a level of uniformity that is greater than a level achievable by random mixing.

As used herein, the term "interactive mixture" means a mixture of a first powder having a first average particle size and a second powder having a second average particle size that is larger than the first average particle size, wherein all, substantially all or at least 90% of the particles of the first particles interact with and adhere to at least one of the plurality of the particles of the second powder. In one embodiment, an ordered mixture is also an interactive mixture.

As used herein, the term "average particle size" means the $D_{50}$. The term $D_{50}$ means that 50 vol % of the particles have a diameter that is smaller than this, and 50 vol % of the particles have a diameter that is larger than this. The average particle size may be measured using standard laser diffraction particle sizing techniques known in the art. One example of an instrument to measure the particle size of the dry powders is the Masteresizer 2000, manufactured by Malvern Instruments Ltd (Worcestershire, UK.).

As used herein, the term "Carr's index" means a dimensionless parameter "C" used to characterize the flowability of a substance, such as a powder, where $C=1-(B/T)$, B is the bulk density of the substance and T is the tapped density of the substance. The Carr's Index can be expressed as a percentage, e.g., if C=0.5, the Can's Index can be expressed as 50%. The bulk density is equal to mass per volume (g/cc) of a sample before being tapped and the tapped density is equal to the mass of a sample divided by the volume of the sample after the sample is tapped for 2000 cycles in a Vankel Tap density instrument.

As used herein, the term "direct compression" or "directly compressing" means a compression of, or compressing, a powder into a tablet without an intermediate granulation process.

Pharmaceutical tablets can be formed by compressing a mixture that comprises a spray dried dispersion (SDD) and one or more excipients, such as a glidant. The SDD can include one or more of the active agents and one or more excipients, such as a polymer. Some spray-drying processes can produce a very fine powdered SDD wherein at least some and/or most of the particles include both an active agent and an excipient.

SDDs having fine particles, such as less than 50 μm in average particle diameter, can have poor flow characteristics. Poor flowability of an SDD can lead to difficulties in handling and compressing the SDI). For example, poor flowability of the SDI) can lead to inconsistent flow through processing equipment and/or inconsistent or incomplete filling of tablet or capsule dies, which can lead to delivery of inconsistent active agent dosages.

To improve the flow characteristics of an SDD, the SDDs are typically subjected to granulation processes that increase the particle size of the SDI). Exemplary granulation processes can include wet granulation and dry granulation, such as via roller compaction. These granulation processes, however, can be undesirable for various reasons. For example, dry granulation can result in decreased compressibility of the SDD, which can make forming a tablet from the SDD more difficult. Furthermore, elimination of granulation processes can save time and reduce manufacturing cost. It is therefore desirable to eliminate the need to include a granulation process when forming a pharmaceutical tablet from an SDD.

Exemplary processes of forming a pharmaceutical tablet from an SDD without a granulation process can include blending the SDD with a glidant using high-shear mixing prior to forming the tablet. Typically, one or more additional excipients are also mixed with the SDD and/or the glidant prior to forming the tablet.

Generally, as the average particle diameter, or size, of a powder, such as the SDD, decreases, the flowability of the powder can decrease and the powder can be more likely to clump or flow unevenly. It can therefore be more desirable to improve the flowability of the SDD when the SDD comprises finer particles. In some exemplary methods, the SDD can comprise very fine particles, such as particles having an average particle diameter that is less than 50 µm, less than 40 µm, less than 30 µm, less than 20 µm, from 2 µm to 50 µm, from 5 µm to 50 µm, from 10 µm to 50 µm, and/or from 20 µm to 50 µm.

In addition to particle size, the flow characteristics of the SDI) can also be dependent on the bulk specific volume of the SDD. The bulk specific volume of a powder is the inverse of the bulk density of a powder and can be measured as the volume occupied by a unit mass of the powder, such as in cubic centimeters per gram, when the powder is poured into a container, such as a graduated cylinder. Generally, the lower the bulk specific volume of a powder, the better the flowability of the particles. Improving the flowability of the SDD can therefore be more desirable for an SDD having a higher bulk specific volume. For example, in some exemplary methods, the SDI) can have a bulk specific volume greater than or equal to 3 cc/g, greater than or equal to 5 cc/g, greater than or equal to 8 cc/g, from 3 to 5 cc/g, and/or from 3 to 8 cc/g.

The average particle size of a glidant can be smaller than the average particle size of an SDD. For example, in some exemplary methods, the glidant can have an average particle diameter of less than 40 µm, less than 20 µm, less than 10 µm, less than 1 µm, less than 100 nm, and/or less than 50 nm. In some exemplary methods, the average particle diameter can be from 20 nm to 50 nm. In some cases, the glidant can comprise particles that tend to form secondary particles, or clusters, that have a greater diameter than the particles. For example, glidant particles having an average diameter of from 20 nm to 50 nm can form clusters that can have an average diameter of greater than or equal to 1 µm, greater than or equal to 20 µm, and/or from 1 µm to 20 µm.

In some exemplary methods, the glidant comprises clusters of particles prior to the high-shear blending and at least some, a majority, and/or substantially all of the clusters are broken apart into sub-clusters and/or individual particles during the high-shear mixing. In some examples, the extent to which the clusters are broken apart during high-shear mixing can be related to the Froude Number. For example, a higher Froude Number can result in the cluster being broken apart to a greater extent.

The specific surface area of the glidant can also affect the flowability of the blend after the high-shear mixing. Specific surface area can be measured as the total surface area per unit of mass, such as in $m^2/g$. The total surface area of a powder can be calculated from the particle size distribution of the powder or by using gas adsorption, as is well known in the art. For example, in some exemplary methods, increased specific surface area of the glidant can result in improved flowability of the blend. In one exemplary method, the glidant can have specific surface areas from 50 $m^2/g$ to 600 $m^2/g$. The ratio of surface area to diameter of the particles of the glidant can also be related to improved flowability of the blend.

The glidant particles can also have a high bulk specific volume. For example, in some exemplary methods, the glidant can have a bulk specific volume greater than or equal to 10 cc/g, greater than or equal to 15 cc/g, greater than or equal to 20 cc/g, from 10 to 40 cc/g, and/or from 20 to 40 cc/g.

The glidant particles can be significantly finer than the particles of the SDD. For example, in some exemplary methods, the ratio of the average particle diameter of the SDD to the average particle diameter of the glidant (the SDD-glidant size ratio) can be greater than or equal to 5, greater than or equal to 10, and/or greater than or equal to 20. The SDD-glidant size ratio can be related to the flow characteristics of the blend formed from high-shear mixing of the SDI) and the glidant. For example, the flow characteristics of the blend can improve as the SDD-glidant size ratio increases. In other examples, the flow characteristics of the blend can be most desirable when the SDD-glidant size ratio is within a range, such as greater than or equal to 5, 10 or 20, from 5 to 20, and/or from 5 to 10.

High-shear mixing of the SDD and the glidant can increase the uniformity of the mixed particles, such as producing an ordered mixture and/or an interactive mixture.

A blend of the SDD and the glidant using high-shear mixing can have improved flowability, as measured by Carr's Index, compared to the flowability of the SDD alone. In general, the lower the Can's Index, the better the flowability of the substance. For example, in some exemplary methods, a blend of the SDD and the glidant using high-shear mixing can have can have a Can's Index of less than 40% and/or less than 35%, while the SDD alone can have a Can's Index of greater than 40% and/or greater than 45%. In one specific example, the SDD alone has a Can's Index of 47.4% and a mixture of the SDD with several excipients, including a glidant, has a Carr's Index of 34.6%. In this example, the SDI) mixed at low shear with the same excipients except for the glidant has a Can's Index of 44.4%, reflecting the strong correlation between the glidant, high-shear mixing, and improved flowability.

A powder having a lower Can's Index can also be easier to compress into a tablet. In some exemplary methods, a mixture having a Can's index greater than 40%, for example, can be difficult to compress into a tablet. For example, a tablet formed from a mixture having a high Carr's Index can be more likely to crack, fracture, or otherwise fail to stick together or maintain a tablet form after compression. Adding a glidant to the SDI) with high-shear mixing can produce a mixture having a low Carr's Index, such as below 40% and/or 35%, that is suitable for direct compression. This allows direct compression of the SDD without the need to include an intermediate granulation process to decrease the Can's Index of the mixture to a suitable level.

In some exemplary methods, a tablet formed from the method can comprise a high-loading of SDD. For example, some methods can produce a tablet having more than 50% SDD by weight, more than 60% SDD by weight, more than 70% SDD by weight, and/or more than 80% SDD by weight. Such high-loading can be achieved by reducing the relative proportion of excipients added to the SDD prior to formation of the solid dosage form. Methods including high-shear mixing of a glidant with the SDD can reduce the amount of glidant needed to achieve a sufficiently low Carr's Index to form a tablet that maintains its form without cracking or fracturing. Less glidant is needed when using high-shear mixing compared to other mixing methods because the high-shear mixing distributes the glidant particles more uniformly among the SDD particles, thereby requiring fewer total glidant particles per volume of SDD. High-shear mixing can also enable the use of finer glidant particles such that each particle weighs less and the overall weight of the glidant in the mixture is reduced. In addition, the glidant can also act as a lubricant and reduce the need to add additional excipients to lubricate the mixture. Thus, the inclusion of high-shear mixing of the glidant with the SDD can reduce to weight of the excipients added to the SDD of enable higher loading of SDD in a tablet.

In some exemplary methods, a tablet formed from the method can be fast-dissolving and/or fast-disintegrating when orally ingested or subjected to a gastric or intestinal buffer.

In addition, tablets formed from a mixture that included a glidant blended with the SDD using high-shear mixing can be substantially completely disintegratable or disintegratable in less than 30 minutes, less than 15 minutes, less than 10 minutes, and/or less than 5 minutes after oral ingestion.

It should be understood that the many exemplary methods described herein can be similarly applied to forming a capsule or other dosage form similar to tablets for a SDD, and this disclosure is intended to include all such alternative methods. One of ordinary skill will understand that the increased flowability and fast-disintegration in vivo that results from the high-shear mixing of an SDD with a glidant is beneficial to forming capsules as well as tablets.

Methods described herein can provide one or more the following exemplary advantages:
1. Lower process times and costs, by elimination of the granulation process. Process is cheaper and easier without granulation.
2. Lower risk of batch failure or manufacturing delays, due to less complex process and unit operations.
3. Less risk of compression issues, due to poor compressibility such as that which can occur with a dry granulation process.
4. Possibility for enabling a straightforward, continuous processing train. Granulation causes disruption of the processing.

Example 1

Formation of Spray-Dried Dispersion (SDD)

The following process was used to form a spray-dried dispersion (SDD) containing 25 wt % phenytoin and 75 wt % hydroxypropyl methylcellulose acetate succinate (HPMCAS-MG) (AQOAT-MG, ShinEtsu, Tokyo, Japan). First, a spray solution was formed by dissolving 1.5 wt % phenytoin and 4.5 wt % HPMCAS-MG in 94 wt % acetone. The solution was added to a 2 liter nitrogen-pressurized feed tank and delivered to an intermediate size spray dryer equipped with a 7.6-cm chamber extension and a pressure atomizer (Schlick 2.0 Pressure Swirl [Düsen-Schlick GmbH, Coburg, Germany]). Atomization pressure was 105 psig, and the feed rate was about 30 g/min. Heated nitrogen drying gas was introduced at a flow rate of 515 g/min. The inlet temperature was 103° C. and the outlet temperature was 50° C. A perforated stainless steel plate uniformly distributed the heated nitrogen drying gas and provided plug flow of drying gas through the drying chamber. The spray-dried dispersion (SDD) formed by this process was collected using a high-efficiency 15.2-cm cyclone separator. A filter collected particles not captured by the cyclone.

The dispersion formed using the above procedure was post-dried using a Gruenberg single-pass convection tray dryer operating at 40° C./10% RH for 17 hours. The particle size of the dispersion was measured using a Malvern particle size analyzer (Worcestershire, UK), and the $D_{50}$ was found to be 25 μm (50 vol % of the particles have a diameter that is smaller than this).

Tablet Formation

Two 40 gram tablet lots were prepared to identify the influence of Colloidal Silicon Dioxide (CSD), a glidant, on the effects of a the above spray dried dispersion (SDD) in a directly compressible tablet formulation.

Table 1 details the composition of the 800 mg tablets prepared. Two tablet formulations were made. Lot 1 was the example formulation (using CSD), while lot C was the control formulation (containing no CSD). Tables 2 and 3 outline the materials and equipment used during production and testing of the tablets.

TABLE 1

Composition of Tablet Lots Prepared

| Component | Lot 1 (Example Formulation) (mg/tablet) | Lot C (control lot) (mg/tablet) |
|---|---|---|
| 25% Phenytoin:HPMCAS-MG, SDD | 400 | 400 |
| Microcrystalline Cellulose (Avicel PH101, NF) | 168.99 | 179.02 |
| Lactose Monohydrate Regular 310, NF | 168.99 | 168.99 |
| Croscarmellose sodium (Ac-Di-Sol, NF) | 47.96 | 47.96 |
| Colloidal silicon dioxide (Cab-O-Sil, M5P, NF) | 10.03 | 0 |
| Magnesium stearate (Vegetable grade, USP) | 4.03 | 4.03 |
| TOTAL | 800 | 800 |

TABLE 2

Material List

| Component | Trade Name | Function | Manufacturer |
|---|---|---|---|
| 25% A Phenytoin:HPMCAS-MG | NA | SDD | Bend Research |
| Microcrystalline Cellulose | Avicel PH 101, NF | Ductile Filler | FMC |
| Lactose Monohydrate | Lactose Monohydrate Regular 310, NF | Brittle Filler | Foremost |
| Croscarmellose Sodium | Ac-Di-Sol, NF | Disintegrant | FMC |

TABLE 2-continued

Material List

| Component | Trade Name | Function | Manufacturer |
|---|---|---|---|
| Colloidal Silicon Dioxide | Cab-O-Sil M5P | Glidant | Cabot |
| Magnesium Stearate Vegetable grade, USP | Magnesium Stearate, USP | Lubricant | Mallinckrodt |

TABLE 3

Equipment List

| Component | Model | Manufacturer | Calibration Date |
|---|---|---|---|
| Analytical Balance | CP224S | Sartorius | June 2011 |
| Mixer | Turbula Mixer | Glenn Mills | N/A |
| Mill | Quadro Comil 193 AS | Quadro | N/A |
| Tablet Press | F Press | Manesty | N/A |
| Tablet Tooling | 0.3577 × 0.7154" Modified Oval | Natoli | N/A |
| Calipers | Mitutoyo Absolute | Mitutoyo | N/A |
| Hardness Tester | Model 6D | Schleuniger | N/A |
| Disintegration Tester | ZT 71 | Erweka | N/A |
| Tap Volumeter | | Vankel | N/A |

Blending and Compression

A modified geometric dilution blend method was chosen as a starting base for development. FIG. 1 outlines the processes used for blending and compression. More specifically, the manufacturing processes used for blending and compression, as shown in FIG. 1, include:
1. Add 25% A Phenytoin:HPMCAS-MG SDD to the blender. Remove a portion of subdivided SDD (approximately 3 to 10 times the weight of required colloidal silicon dioxide) into an LDPE bag or the equivalent, followed by the addition of colloidal silica dioxide (to the bag) to provide for the initial dispersing of the glidant. Manually mix for approximately 30 seconds to 2 minutes and then pass the mixture through a No. 30 mesh screen into the main product container along with any remaining material on the screen to complete the initial dispersing of the glidant. Transfer the blend to an appropriate sized amber bottle.
2. Sequentially add microcrystalline cellulose, lactose monohydrate, and croscarmellose sodium into the amber bottle from step 1. Blend for 15 minutes at the default mixing speed of the turbula mixer.
3. High-shear mix the initial blend from Step 2 by passing it through a Comil 197 (or equivalent) equipped with a 0.032-inch (032R) screen and 1601 impeller into an appropriate container. Adjust the impeller speed to 2000 rpm. Since the Comil has a chamber diameter of 2.2 inches, the Froude Number is about 125.
4. Add the blend from Step 3 into the blender, removing a portion (approximately 3 to 10 times the weight of required magnesium stearate) into an LDPE bag, or equivalent, followed by the addition of magnesium stearate (into the bag). Manually mix for approximately 30 seconds to 2 minutes to provide for the initial dispersing of the magnesium stearate and then pass the mixture through a No. 30 mesh screen into the main product container along with any remaining material on the screen to complete the initial dispersing of the lubricant. Blend for 5 minutes at the turbula mixer's default rpm.
5. Remove the appropriately sized amber bottle from the turbula mixer.
6. Using a single station F press (Manesty F press or equivalent), compress the tablets using the parameters shown in Table 4.

TABLE 4

Tableting Parameters

| Parameter | Value |
|---|---|
| Tooling size | 0.3577 × 0.7154 inch, modified oval |
| Tablet weight | 800.0 mg |
| Tablet hardness | 16 to 20 kP |
| Approximate main compression force | 20 to 25 kN |

Disintegration Testing Method

Each tablet lot was tested in both gastric buffer and intestinal buffer using the method outlined below. Table 5 displays the disintegration times that were recorded for this testing.
1. Fill 1 liter test beaker with 700 mL of 0.01M (mol/L) Hydrochloric Acid (HCL) pH 2.2 gastric buffer or 50 mM $H_2KPO_4$ pH 6.8 intestinal buffer.
2. Place test beaker into a water bath set to 37.5° C.; allow adequate time for the buffer to come to temperature.
3. Attach disintegration basket with sensors to the disintegration tester. Make sure that each appropriately labeled sensor (1-6) is in the corresponding cylinder in the basket.
4. Adjust basket sensors to read between −1 and 1 using the adjust function on the disintegration tester.
5. Remove the required number of sensors from the basket and place n=1 of each tablet lot being tested into a separate cylinder in the disintegration basket.
6. Once the buffer solution has reached temperature begin the disintegration tester and a timer.
7. Record the time taken for the tablets to disintegrate in the buffer solution.

TABLE 5

Disintegration Test Results

| Buffer Used | Lot 1 Time elapsed (sec) | Control Lot Time elapsed (sec) |
|---|---|---|
| .01M HCL | 16 | 20 |
| 50 mM $H_2KPO_4$ | 18 | 16 |

Carr's Index Testing Method

The flowability for each tablet blend and the original SDD was also evaluated using the Can's Index calculated using bulk and tap density. The method is given below. Table 6 displays the Carr's index for each lot.

Bulk Density Method:
1. Obtain the tare weight of graduated cylinder and record.
2. Record total volume of cylinder (i.e. 10 cc or 100 cc)
3. Carefully add granulation or intermediate to a graduated cylinder being careful to handle as little as possible.
4. Obtain the weight of the cylinder with the sample and record.

5. Obtain the volume that the sample takes up in the cylinder.
6. To calculate the Bulk density take the weight of the sample and divide that by the volume recorded.

Bulk Density=Weight of Sample (g)÷Volume of Sample (cc)

Tapped Density Method:
1. Take the above Bulk Density sample in the cylinder and place in the Vankel Tap density instrument.
2. Tap for 2000 cycles.
3. Obtain the volume that the sample takes up in the cylinder and record.

Tapped Density =

Weight of Sample (g)÷Volume of Sample after 2000 Tap Cycles (cc)

Carr's Index Determination:

$$C = 100 \times \left(1 - \frac{\rho_B}{\rho_T}\right)$$

Where $\rho_B$ is equal to the bulk density and $\rho T$ is equal to the tapped density.

TABLE 6

Carr's Index Results

| Component | Formulation | Bulk Specific Volume (cc/g) | Tapped Specific Volume (cc/g) | Carr's Index |
|---|---|---|---|---|
| SDD | 25% A Phenytoin:HPMCAS SDD (untreated) | 5.78 | 3.04 | 47.4% |
| Control Lot | Control Formulation (made without CSD) | 3.75 | 2.08 | 44.4% |
| Lot 1 | Formulation made with CSD | 3.04 | 1.99 | 34.6% |

Generally, the lower the Carr's index, the better the flow properties of the powder.

Example 2

The following is an alternative method for forming a pharmaceutical tablet from an SDD:
1. Spray dry the active agent and a polymer to obtain a SDD to form particles having a bulk specific volume of 3-5 cc/g.
2. De-lump the colloidal silicon dioxide (CSD), for example through a #40 US Mesh screen.
3. Dilute the CSD by adding all of it to a small portion of the SDD (e.g., 3-10× the weight of the CSD), and passing the mixture through a #20 Mesh screen.
4. Add the screened mixture to the remaining bulk of SDD powder, hand blend or blend for about five minutes in a low-shear blender (e.g., twin shell or bin blender), and then pass through a high-shear mill (e.g., Comil with a 0.032" screen) or blend in a high-shear mixer (e.g., Gral, TK Fielder, Glatt Powerex).
5. Repeat step 4 if necessary (e.g., "2-pass" Comil process).
6. Add the remainder of the tablet excipients (e.g., filler, disintegrant) except the lubricant and blend in a low-shear blender.
7. Add the lubricant to the mixture and blend in a low-shear blender.
8. Compress tablets on a rotary tablet press or encapsulate capsules using either a tamping pin or dosator style machine.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for forming a pharmaceutical dosage form, comprising:
   providing a spray-dried dispersion comprising particles wherein the particles comprise an active agent and a polymer, the dispersion having an average particle diameter of less than 50 μm;
   forming an ordered mixture consisting of the spray-dried dispersion and a glidant, the ordered mixture being formed by dry high-shear mixing a blend comprising the spray-dried dispersion and the glidant, wherein the glidant is selected from a group consisting of colloidal silicas, colloidal silicon dioxide, fumed silica, talc, starch, and magnesium aluminum silicates, and the glidant having an average particle diameter of less than or equal to one-fifth the average particle diameter of the dispersion after high-shear mixing; and
   forming the pharmaceutical dosage form by at least one of directly compressing the ordered mixture to form a tablet and encapsulating the ordered mixture to form a capsule.

2. The method of claim 1, wherein the glidant in the ordered mixture has an average particle diameter of less than or equal to one-tenth of the average particle diameter of the dispersion in the ordered mixture after high-shear mixing.

3. The method of claim 1, wherein the glidant in the ordered mixture has an average particle diameter of less than or equal to one-twentieth of the average particle diameter of the dispersion in the ordered mixture after high-shear mixing.

4. The method of claim 1, wherein the ordered mixture is an interactive mixture.

5. The method of claim 1, wherein the dispersion has an average particle diameter of less than 30 μm prior to high-shear mixing.

6. The method of claim 1, wherein the dispersion comprises at least 50% of the tablet by weight.

7. The method of claim 1, wherein the high-shear mixing has a Froude Number greater than or equal to 1.

8. The method of claim 1, wherein the glidant comprises colloidal silicon dioxide, fumed silica, or mixtures thereof.

9. A method of preparing a pharmaceutical dosage form, comprising:
   providing a spray-dried dispersion comprising particles wherein the particles comprise an active agent and a polymer, the dispersion having an average particle diameter of less than 50 μm;
   forming an ordered mixture consisting of the dispersion and a glidant using dry high-shear mixing, the glidant being selected from a group consisting of colloidal silicas, colloidal silicon dioxide, fumed silica, talc, starch, and magnesium aluminum silicates, and the ordered mixture having a Carr's Index of less than 40%; and forming the pharmaceutical dosage form by directly compressing the ordered mixture to form a tablet or encapsulating the ordered mixture to form a capsule.

10. The method of claim 9, the ordered mixture having a Carr's Index of less than or equal to 35%.

11. The method of claim 9, wherein the glidant in the ordered mixture has an average particle diameter of less than or equal to one-fifth of the average particle diameter of the dispersion in the ordered mixture after high-shear mixing.

12. The method of claim 9, wherein the glidant in the ordered mixture has an average particle diameter of less than or equal to one-tenth of the average particle diameter of the dispersion in the ordered mixture after high-shear mixing.

13. The method of claim 9, wherein the glidant in the ordered mixture has an average particle diameter of less than or equal to one-twentieth of the average particle diameter of the dispersion in the ordered mixture after high-shear mixing.

14. The method of claim 9, wherein the ordered mixture is an interactive mixture.

15. The method of claim 9, wherein the glidant comprises colloidal silicon dioxide, fumed silica, or mixtures thereof.

16. A method for forming a pharmaceutical dosage form, comprising:
provide a spray-dried amorphous dispersion comprising particles, the particles comprising an active agent and a polymer, the dispersion having an average particle diameter of less than 50 μm;
forming a blend consisting of the dispersion and a powdered glidant using dry high-shear mixing, the glidant being selected from a group consisting of colloidal silicas, colloidal silicon dioxide, fumed silica, talc, starch, and magnesium aluminum silicates, the high-shear mixing having a Froude Number greater than 0.2; and
forming the pharmaceutical dosage form by at least one of directly compressing the blend to form a tablet and encapsulating the blend to form a capsule.

17. The method of claim 16, wherein the high-shear mixing comprises an impeller rotation rate of at least 1000 RPM.

18. The method of claim 16, wherein the glidant comprises colloidal silicon dioxide, fumed silica, or mixtures thereof.

* * * * *